(12) United States Patent
Ranzoni et al.

(10) Patent No.: US 8,981,772 B2
(45) Date of Patent: Mar. 17, 2015

(54) ROTATING MAGNETIC FIELD FOR IMPROVED DETECTION IN CLUSTER ASSAYS

(75) Inventors: Andrea Ranzoni, Eindhoven (NL); Menno Willem Jose Prins, Rosmalen (NL); Mikhail Mikhaylovich Ovsyanko, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 905 days.

(21) Appl. No.: 13/060,804

(22) PCT Filed: Sep. 4, 2009

(86) PCT No.: PCT/IB2009/053868
§ 371 (c)(1),
(2), (4) Date: Feb. 25, 2011

(87) PCT Pub. No.: WO2010/026551
PCT Pub. Date: Mar. 11, 2010

(65) Prior Publication Data
US 2011/0156701 A1 Jun. 30, 2011

(30) Foreign Application Priority Data
Sep. 5, 2008 (EP) .................... 08105253

(51) Int. Cl.
*G01R 33/02* (2006.01)
*G01N 33/553* (2006.01)
(Continued)

(52) U.S. Cl.
CPC ........ *G01N 33/54333* (2013.01); *G01N 27/745* (2013.01)
USPC .......................................... 324/244; 436/526

(58) Field of Classification Search
USPC ............................................... 324/244.1, 244
See application file for complete search history.

(56) References Cited

U.S. PATENT DOCUMENTS 4,498,785 A * 2/1985 de Bruyne .................... 366/274
5,781,985 A * 7/1998 Nakaishi et al. ............. 29/602.1
(Continued)

FOREIGN PATENT DOCUMENTS

JP 2006247535 A 9/2006
WO 03028856 A1 4/2003
(Continued)

OTHER PUBLICATIONS

Yellen, Benjamin B. et al "Traveling Wave Magnetophoresis for High Resolution Chip Based Separations", Lab on a Chip, vol. 7, pp. 1681-1688; Sep. 2007.
(Continued)

*Primary Examiner* — Bot Ledynh

(57) ABSTRACT

In a method of performing a cluster assay, a suspension (14) of superparamagnetic particles in a fluid to be analyzed is provided, wherein the superparamagnetic particles are coated with a bioactive agent. The particles are then allowed to form clusters due to an analyte present within the fluid. Subsequently, clusters of superparamagnetic particles are selectively actuated by applying a rotating magnetic field, wherein the amplitude of the magnetic field varies over time. Finally, the selectively actuated clusters are detected. An apparatus for performing a cluster assay comprises means for accommodating a sample (12) and means for applying a rotating magnetic field (11), the magnetic field being adapted for selectively actuating clusters of superparamagnetic particles. The apparatus further comprises means for detecting the selectively actuated clusters.

17 Claims, 6 Drawing Sheets

(51) Int. Cl.
*G01N 33/543* (2006.01)
*G01N 27/74* (2006.01)

(56) References Cited

U.S. PATENT DOCUMENTS

| | | |
|---|---|---|
| 6,716,642 B1 | 4/2004 | Wu |
| 2004/0126903 A1* | 7/2004 | Garcia et al. ................ 436/526 |
| 2007/0215553 A1 | 9/2007 | Yellen |

FOREIGN PATENT DOCUMENTS

| | | |
|---|---|---|
| WO | 2004012836 A2 | 2/2004 |
| WO | 2008072156 A2 | 6/2008 |
| WO | 2008075285 A1 | 6/2008 |
| WO | 2009037636 A1 | 3/2009 |

OTHER PUBLICATIONS

Baudry, J. et al "Acceleration of the Recognition Rate Between Grafted Ligands and Receptors with Magnetic Forces" Proc. Nat'l Acad. Sci. vol. 103, No. 44, Oct. 2006, pp. 16076-16078.

Tanaka, K. et al "Rapid and Reagent-Saving Immunoassay using Innovative Stirring Actions of Magnetic Beads in Microreactors in the Sequential Injection Mode" Science Direct, Talanta, vol. 68, 2005, pp. 437-441.

Vuppu, Anil K. et al "Phase Sensitive Enhancement for Biochemical Detection using Rotating Paramagnetic Particle Chains" Journal of Applied Physics, vol. 96, No. 11, Dec. 2004, pp. 6831-6838.

* cited by examiner

ROTATING MAGNETIC FIELD FOR IMPROVED DETECTION IN CLUSTER ASSAYS

FIELD OF THE INVENTION

The present invention is directed to a method of performing a cluster assay and to an apparatus for performing such a cluster assay.

BACKGROUND OF THE INVENTION

Tests in in vitro diagnostics can have several assay formats. Cluster assays are a class of assays in which the amount of formed particle clusters is indicative of the presence and/or concentration of biological components in the sample. Cluster assays are attractive because of the rapid bulk kinetics, ease of fabrication and low costs.

The main issue with cluster assays is the lack of sensitivity. One way to improve the sensitivity is by performing cluster assays with magnetic particles. An advantage of using magnetic particles is that field-induced chains can be formed during incubation. This has, e.g., been shown by Baudry et al. "Acceleration of the recognition rate between grafted ligands and receptors with magnetic forces", Proc. Natl. Acad. Sci. p. 16076).

One important challenge when performing cluster assays is to detect very low concentrations of clusters in a background of other magnetic particles. Another challenge is to avoid the formation of clusters of non-biological origin, and preferably to even break weakly bound clusters. These challenges are particularly important when magnetic actuation is used during the detection.

SUMMARY OF THE INVENTION

It is an object of the invention to provide a method and an apparatus which allow the detection of very low concentrations of clusters 20 of magnetic particles, also called beads, within the background of other magnetic particles.

A method is provided of performing a cluster assay comprising the steps of:
a) providing a suspension of superparamagnetic particles in a fluid to be analyzed, wherein the superparamagnetic particles are coated with a bioactive agent;
b) allowing the particles to form clusters due to an analyte present within the fluid;
c) selectively actuating clusters of superparamagnetic particles by applying an at least partially rotating magnetic field (B), and
d) detecting the selectively actuated clusters.

Further, an apparatus for performing a cluster assay is provided, comprising:
e) means (12, 15) for accommodating a sample (14);
f) means (1 to 4; 11) for applying an at least partially rotating magnetic field (B), the magnetic field being adapted for selectively actuating clusters of superparamagnetic particles; and
g) means for detecting the selectively actuated clusters.

The present invention is based on the finding that a rotating magnetic field with a generally varying field amplitude can couple selectively to bound clusters 20. If the field characteristics are chosen properly, the field does not rotate larger clusters 20 and it does not generate novel clusters 20 during the actuation.

When exposed to a rotating external magnetic field, superparamagnetic beads can efficiently couple to the magnetic field and rotate together with the field. The rotational behaviour is rather complex and involves three different regimes: initially, the superparamagnetic beads can rotate at the same frequency as the external field, but with a frequency-dependent phase-lag. Once the phase-lag reaches 90 degrees, the bead is experiencing the maximum torque available (at the so-called "breakdown frequency"). If the external frequency is increased further the coupling between the external field and the superparamagnetic beads becomes more and more inefficient and the beads start to slow down. Furthermore, a wiggling rotation of the clusters 20 can be observed: a backward oscillation superimposes the smooth rotation of the superparamagnetic beads. The wiggling rotation appears at frequencies of the magnetic field higher than a critical frequency as described below. At even higher frequencies, the beads are able to rotate again due to the presence of nanometric grains of ferromagnetic material within the superparamagnetic beads.

The present invention is directed to a method of performing a cluster assay using the above-mentioned finding. According to the inventive method, a suspension of superparamagnetic particles in a fluid to be analyzed is provided, wherein the superparamagnetic particles are coated with a bioactive agent. The particles are then allowed to form clusters 20 due to an analyte present within the fluid. The binding of superparamagnetic particles to an analyte is known in the state of the art. Subsequently, clusters 20 of superparamagnetic particles are selectively actuated by applying an at least partially rotating magnetic field, wherein the amplitude of the magnetic field varies over time. The magnetic field can be designed having completely rotating properties or alternatively having partly common properties and partly rotating properties. Finally, the selectively actuated clusters 20 are detected.

The superparamagnetic particles are preferably superparamagnetic beads with a diameter in the range between 10 nm and 10 µm, preferably between 100 nm and 3 µm. The superparamagnetic particles may be coated with any bioactive agent, which is suitable for performing a cluster assay. Typical examples for such a bioactive agent are: antibodies, proteins, cells, DNA, RNA, small molecules, tissues, viruses.

During the step of allowing the particles to form clusters 20, the particles are bound to each other by means of an analyte, which is present within the fluid, which selectively binds to the bioactive agent provided on the surface of the superparamagnetic particles. According to one embodiment, the step is provided by simply setting a predetermined delay time, during which the analyte may interact with the bioactive agent. In another embodiment, the particles are actively supported to form clusters 20, e.g., by means of applying a magnetic field.

Once clusters 20 of superparamagnetic particles have been formed, these clusters 20 are selectively actuated by applying a rotating magnetic field. "Selectively actuating clusters 20" in the context of the present application means to actuate only clusters 20 of certain predetermined characteristics. It is, e.g., preferred to actuate clusters 20 up to a predetermined size only. It is particularly preferred to actuate clusters 20 consisting of two particles only. According to a preferred embodiment, actuating the clusters 20 comprises rotating the clusters 20. Thus, if the characteristics of the rotating magnetic field are chosen properly, one may achieve that only clusters 20 consisting of two particles are rotating, whereas larger clusters 20 do not rotate at all or rotate with another frequency and/or other characteristics.

Therein, the process of selectively actuating, i.e. rotating, clusters 20 of superparamagnetic particles is controlled by applying a rotating magnetic field with a varying field amplitude. For example, the rotating magnetic field may consist of two components, wherein the two components differ in amplitude and phase. According to a preferred embodiment, the ratio between the maximum and minimum amplitudes of the magnetic field is between 1.1 and 10, preferably between 2 and 8, and most preferably between 4 and 6.

It is further preferred, that the angular frequency of the rotating magnetic field is below a critical frequency, wherein the critical frequency is defined as $$f_c = \frac{1}{2\pi} \frac{(1/6)\chi^2 B_{MAX}^2}{28\eta\mu_0}.$$

Therein, $\chi$ is the magnetic susceptibility, $B_{MAX}$ is the amplitude of the external magnetic field and $\eta$ the viscosity of the fluid.

Finally, the selectively actuated clusters 20 have to be detected. This is preferably done using an optical technique. Since the clusters 20 are rotating any light scattering, transmission or reflection is modulated. This modulation may be used to optically detect the rotating clusters 20 only.

The present invention is further directed to an apparatus for performing a cluster assay, in particular for performing a cluster assay according to the above-described method. The apparatus comprises means for accommodating a sample and means for applying a rotating magnetic field, the magnetic field being adapted for selectively actuating clusters of superparamagnetic particles. The apparatus further comprises means for detecting the selectively actuated clusters.

The means for applying a rotating magnetic field preferably comprises several magnetic coils, in particular a quadrupole configuration of four magnetic coils. It is preferred that the ratio between the maximum and minimum amplitudes of the rotation magnetic field is between 1.1 and 10, preferably between 2 and 8 and most preferably between 4 and 6. It is further preferred that the angular frequency of the rotating magnetic field is below the critical frequency, wherein the critical frequency is defined as $$f_c = \frac{1}{2\pi} \frac{(1/6)\chi^2 B_{MAX}^2}{28\eta\mu_0}.$$

The means for detecting the selectively actuated clusters preferably comprises an optical detector (not shown). It is further preferred that the means for detecting comprises a central processing unit adapted to analyze modulations in the detected signal.

These and other aspects of the invention will be apparent from and elucidated with reference to the embodiment(s) described hereinafter.

BRIEF DESCRIPTION OF THE DRAWINGS

FIG. 2b schematically illustrates the driving signals used to drive the coils of the quadrupole configuration of FIG. 2a.

FIG. 6 is a graph showing the numerical derivative of the data shown in FIG. 3a.

FIG. 7b shows a photograph of the apparatus of FIG. 7a.

DETAILED DESCRIPTION OF EMBODIMENTS

Figure 1A:
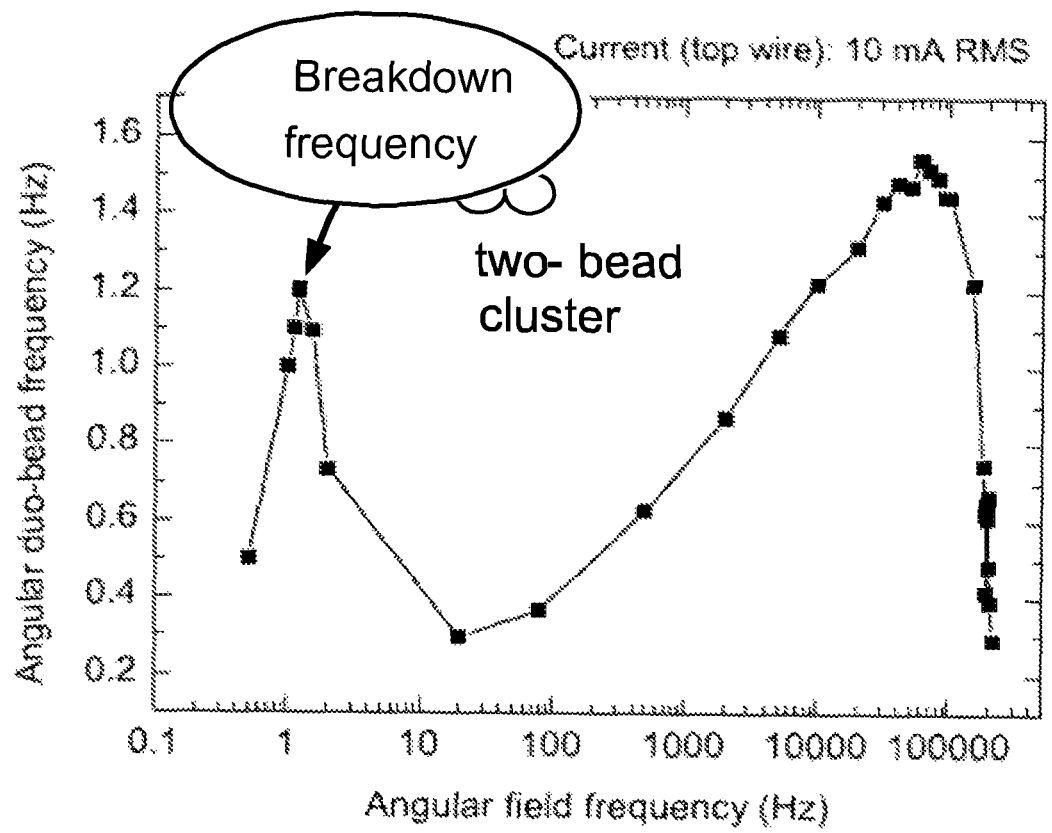
FIG. 1a shows the rotational behaviour of a cluster consisting of two magnetic particles.
Figure 1B:
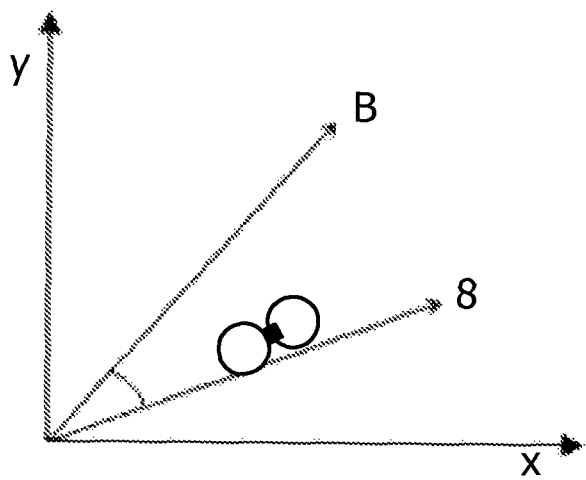
FIG. 1b schematically depicts the phase-lag a of the cluster rotation with respect to the rotation of the external magnetic field.
Figure 2A:
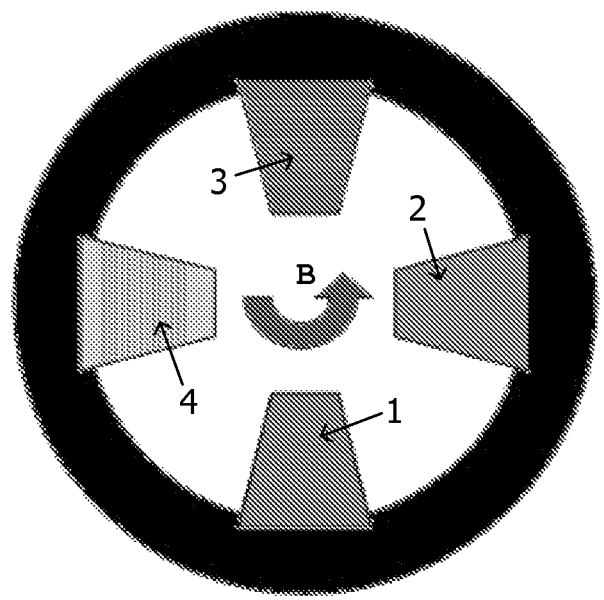
FIG. 2a shows a schematic representation of a quadrupole configuration.
Figure 2B:
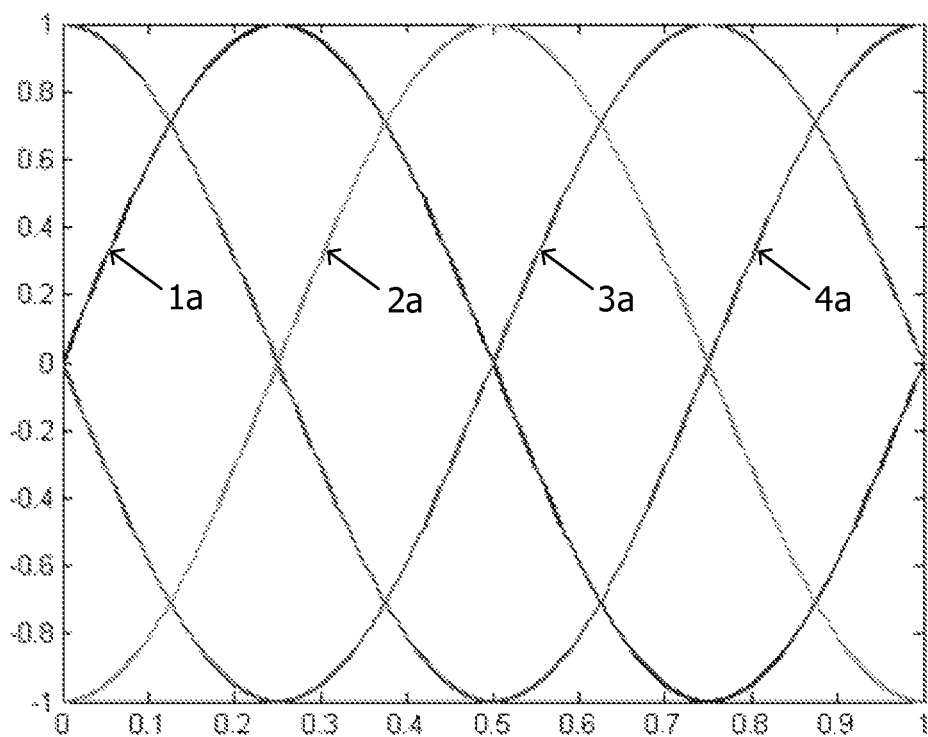

The graph depicted in FIG. 1a shows the angular frequency of a cluster consisting of two particles versus the angular frequency of an externally applied magnetic field. As can be taken from FIG. 1a, the angular frequency of the cluster initially increases with an increase of the angular frequency of the external magnetic field B generated by means of driving signals 1a through 4a applied to coils 1 to 4 of the quadrupole, respectively, as shown in FIGS. 2a and 2b. The configuration according to FIG. 2a comprises four poles 1, 2, 3, 4 arranged at a ring as shown. By activating the four coils 1, 2, 3, 4 of the corresponding poles in a certain manner, for instance as shown in the signal curve in FIG. 2b, a rotational field is generated. This rotating magnetic field is depicted by the arcuate arrow in the middle of the quadrupole. While the amplitudes of the signals characterizing the voltage applied actuating the coils 1, 2, 3, 4 vary in a controlled way the generated magnetic field within the quadrupole rotates. In FIG. 2a sinusoidal signal curves 1a, 2a, 3a, 4a describing activation signals are shown corresponding to the four coils 1, 2, 3, 4. The signal curves can be changed resulting in a different magnetic field. This different magnetic field is referred to as partly rotating magnetic field consisting of a weak component and a strong component. The weak component is either a constant magnetic field, a magnetic field generated by sinusoidal signals, or generated by square wave signals. The strong component is either a magnetic field generated by a sinusoidal signal, or generated by a sequence of pulses. In the contrary the completely rotating magnetic field is a magnetic field generated by sinusoidal signals. The strong component has a signal amplitude up to 10 times higher than the weak component. The signal frequency of the strong component can be different from the signal frequency of the weak component. Up to a first peak, the clusters can rotate at the same frequency as the external field. However, a phase-lag a, which depends on the frequency, arises between the rotation of the cluster and the rotation of the external magnetic field as is schematically shown in FIG. 1b.

At the first peak, which arises at the so-called breakdown frequency (in the present case around 1.2 Hz), the phase-lag a reaches 90 degrees. At this point, the cluster experiences the maximum torque available. Once the angular frequency of the external magnetic field is increased beyond the breakdown frequency, the coupling between the external field and the cluster becomes more and more inefficient which leads to a slowdown of the clusters. In this regime, a wiggling of the clusters is superimposed to the rotation of the clusters.

If the frequency of the external magnetic field is further increased (in the present case beyond a frequency of 20 Hz) the clusters are able to rotate again due to the presence of nanometric grains of ferromagnetic material within the supermagnetic particles. For cluster assay applications only short chains of beads, i.e. small clusters, are of major interest, in particular in a low concentration limit. The clusters all qualitatively behave in the same way as described in FIG. 1a when exposed to an external, uniformly rotating field.

However, if the external rotational field is modulated, a completely unexpected behaviour of the magnetic clusters is observed. In the case of an amplitude modulation the norm of the magnetic field becomes time dependent:

$$B = (B_0\sin(\omega t), B_0\beta\cos(\omega t)) \rightarrow |B|^2 = B_0^2\beta^2\left[1 - \left(1 - \frac{1}{\beta^2}\right)\sin^2(\omega t)\right]$$

Figure 3A:
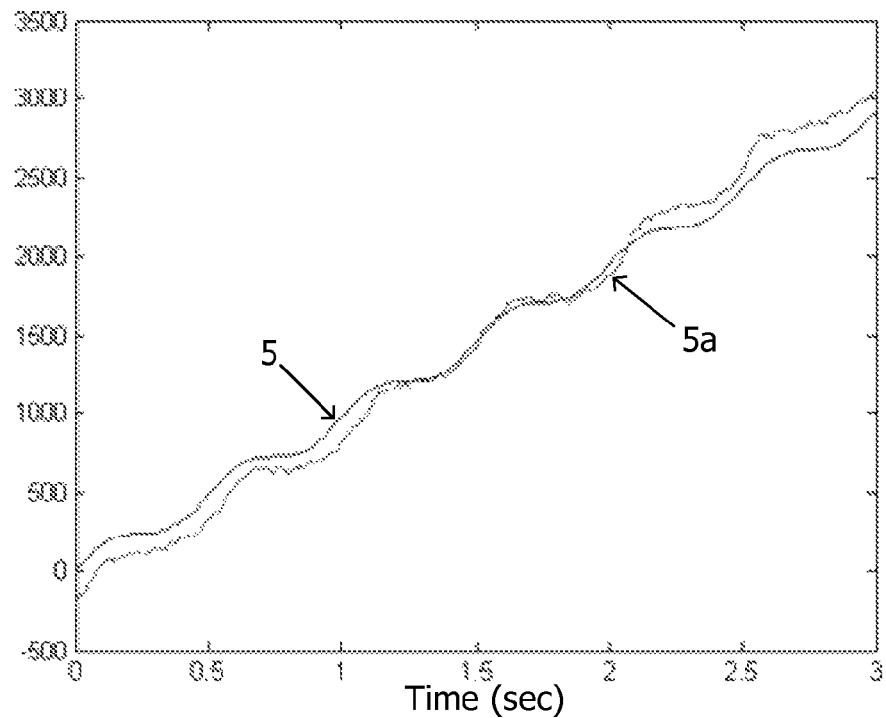
FIG. 3a is a graph showing the cumulative angle versus time in case of a rotating external field with non-uniform amplitude.
Figure 3B:
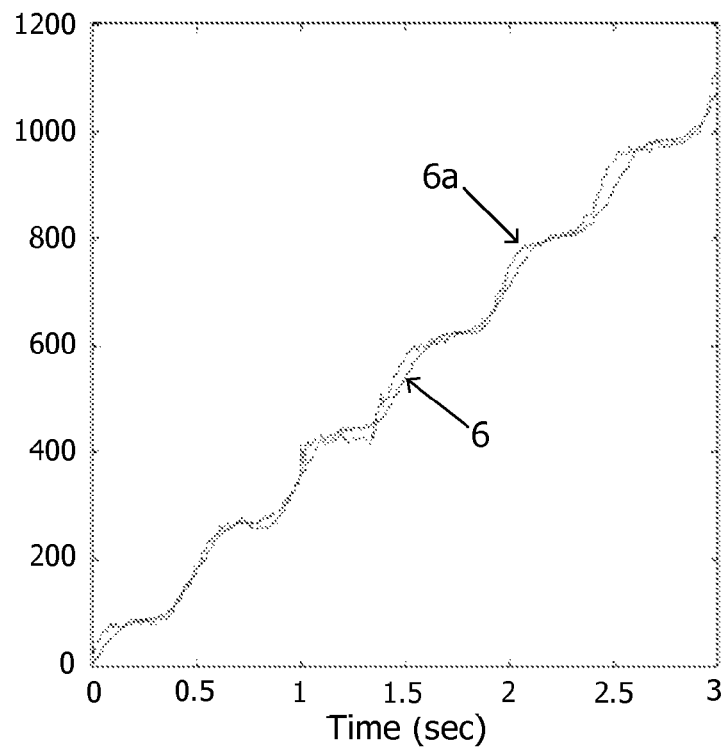
FIG. 3b is a graph showing the cumulative angle versus time in case of a non-uniform angular velocity of the external field.

This implies that all the quantities ruling the rotational behavior of the clusters are now time-dependent leading to a correction in the overall equation of motion. The rotation is no more smooth but characterized instead by sudden increases in the angular velocity in very good agreement with the theoretical predictions. These sudden increases in the angular velocity can be seen, e.g., in FIGS. 3a and 3b. Both Figures show a graph of the cumulative angle versus time. In case of FIG. 3a, the external field is rotated at a frequency of 1 Hz, wherein the amplitude of the rotating field was non-uniform (the ratio between maximum and minimum amplitude was set equal to 5). In the case of FIG. 3b, a non-uniform angular velocity of the external magnetic field was chosen. Both Figures show a theoretical prediction (see curves 5 and 6) as well as experimental results (see curves 5a and 6a).

This particular behavior is observed for all the frequencies below the breakdown frequency. Right above this value the behavior becomes much more irregular: it is still observed but fades off very rapidly. Moreover in this range of frequencies the ability to rotate is highly dependent on the unknown magnetic content of the clusters and the response is really different from cluster to cluster. Analyzing the data (see for example FIG. 3a) is possible to infer that the frequency of the oscillations below the critical frequency is the double of the external frequency (this is consistent with the presence of the time dependent factor in the expression of the square of the module of the magnetic field); these oscillations are always present, even after the breakdown frequency when the wiggling behavior is also present. The frequency of oscillation of the wiggling is $f_{wiggling} = f_{ext} - f_{cluster}$, where $f_{cluster}$ is the overall rotational frequency of a cluster consisting of two particles. These two frequencies are usually different, in this way numerous peaks are observed measuring the cumulative angle above the critical frequency due to the superposition of the wiggling and of the oscillations below the critical frequency.

Figure 4:
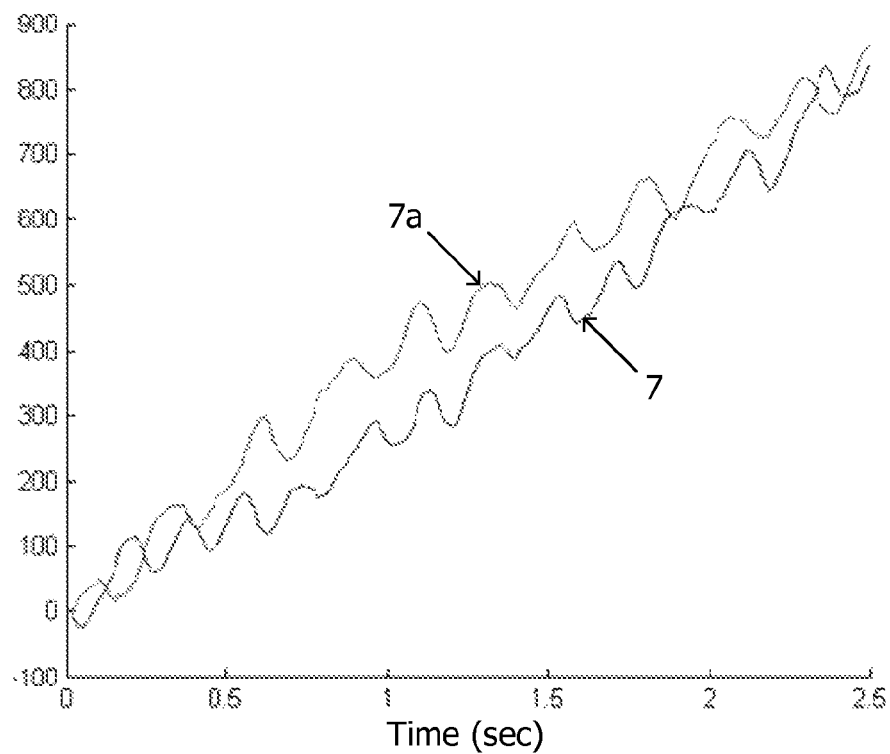
FIG. 4 is a graph showing the cumulative angle versus time for a cluster consisting of two particles in an external field above the critical frequency.
Figure 7A:
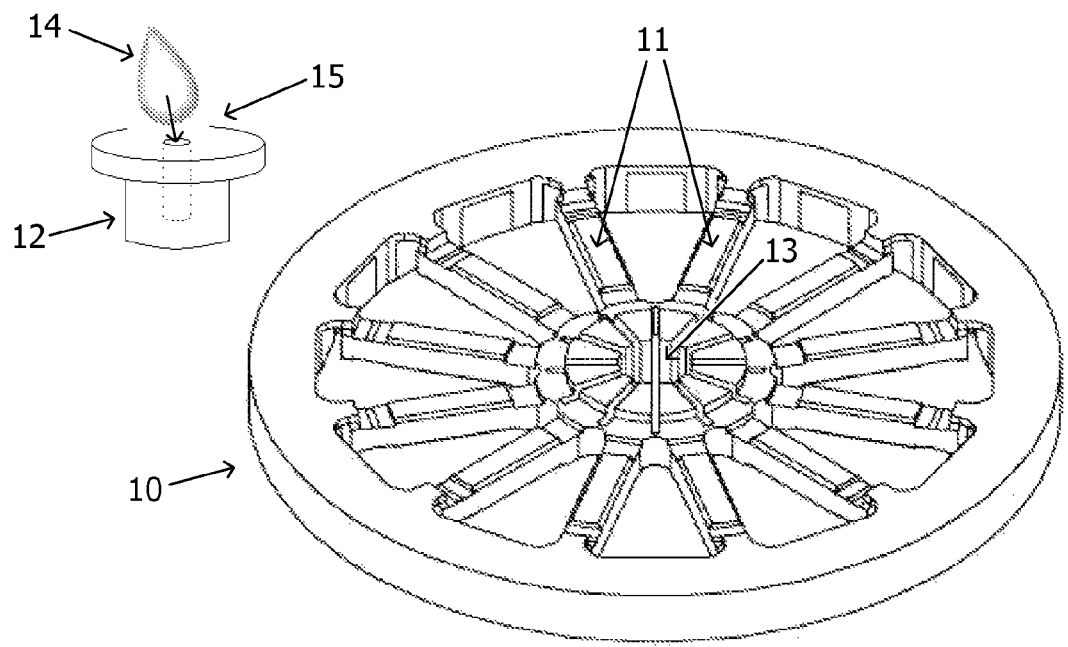
FIG. 7a shows a portion of an apparatus according to a preferred embodiment of the present invention.

An example for the cumulative angle versus time a cluster consisting of two particles experiences in an external magnetic field above the critical frequency is shown in FIG. 4. The critical frequency according to the formula above is 2.87 Hz. Curve 7 in FIG. 4 represents the rotational behaviour of a cluster in an external field rotating with a frequency of 5 Hz, while FIG. 7a represents a cluster in an external frequency of 6.5 Hz. In both cases the clusters consisting of two particles can still rotate, but they behave quite irregular due to the superposition of the wiggling oscillation with the oscillations due to the time dependent factor. Well above that limit none of the clusters is rotating, but just shacking.

If the beads are exposed to a field modulated in phase the results are qualitatively the same. This is due to the fact that the shape of the magnetic field over time is really similar to the case of amplitude modulation. The experiments show that applying a phase shift between 160 and 200 degrees can create the same effect. There are some quantitative differences and it is also much more difficult to reproduce the phenomenon. In some occasions the clusters do not rotate but they prefer to oscillate back and forth. Surprisingly the oscillations seem to be size dependent: the amplitude is different according to the dimensions of the cluster itself. Unfortunately, up to now it is not yet possible to control this phenomenon properly.

Figure 5:
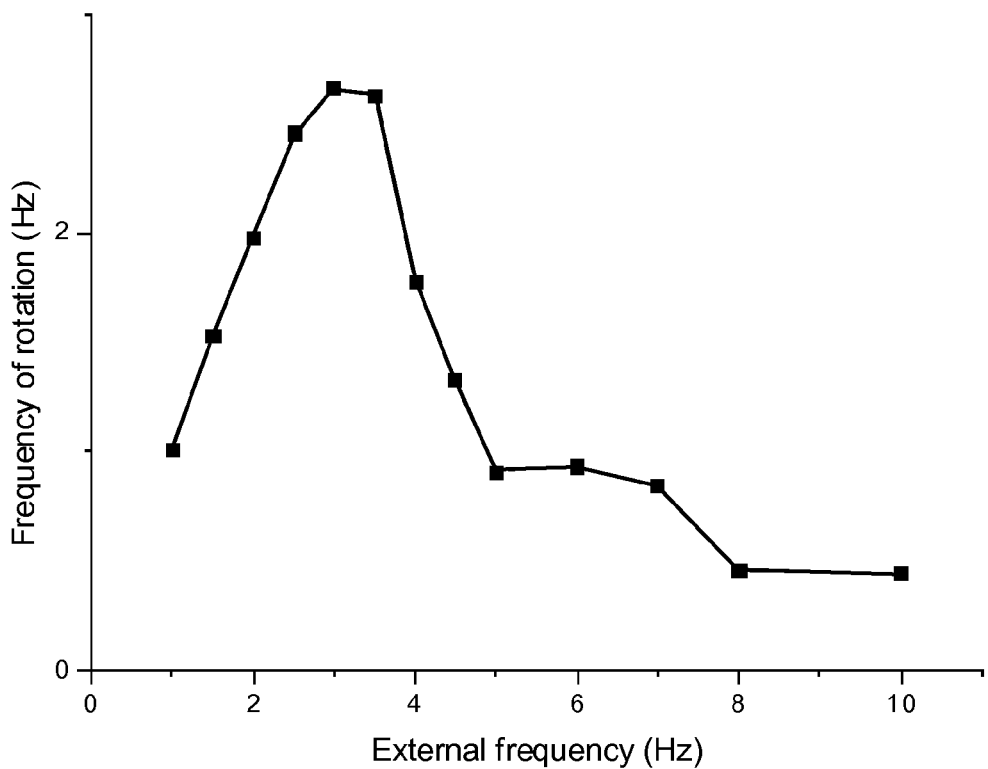
FIG. 5 is a graph illustrating the frequency of particle rotation versus rotational frequency of the external magnetic field.
Figure 6:
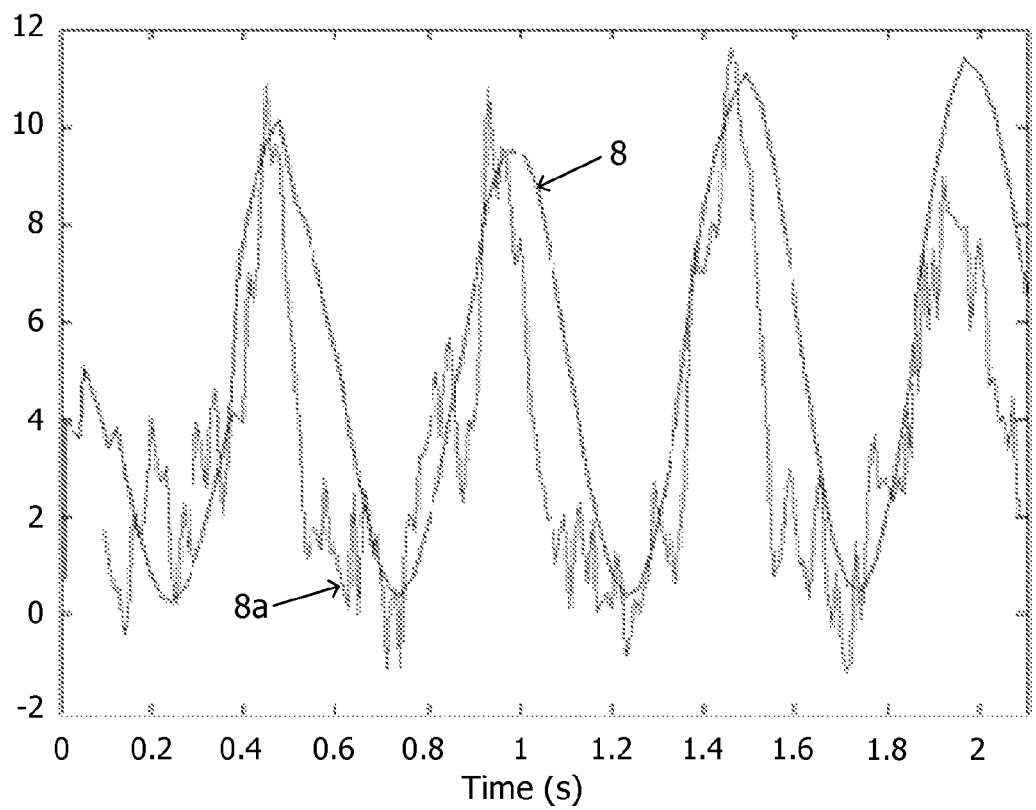

The overall rotational behavior in frequency is depicted in FIG. 5. FIG. 5 shows a graph of the rotational frequency of the rotating cluster versus the frequency of the external magnetic field. In FIG. 5, a clear peak at 2 Hz representing the breakdown frequency is visible. Beyond said breakdown frequency the response decreases rapidly. The breakdown frequency itself is dependent on the size of the beads used.

This effect is observed for different amplitudes of the components of the magnetic field. The lower component seems to be the most important since it must be at least high enough to guarantee the rotation of the smaller clusters and on the same time small enough to prevent the bigger clusters from rotating. In other words the lower component fixes the maximum dimension of the clusters that can be rotated by such a low field. Since the bigger the clusters the bigger must be the field to actuate them, it is indeed possible to tune the value of the lower component so that they do not respond to the field. This tuning process is dependent on a lot of experimental conditions such as the actual implementation of the coils (dimensions, type of magnetic core, number of windings . . . ), the size of the particles used, the hydrodynamic properties of the liquid and the magnetic content of the beads. It has been observed during the experiments that this effect is always present even for strong actuations. It appears that the value of the larger component of the magnetic field is not a crucial parameter in this actuation scheme; the only constraint is that β (i.e. the ratio between the two components) is not so big that the larger component completely outranges the presence of the other component. It is thus preferred that β<10.

The central issue with this new actuation scheme is that the rotational behavior previously described is only observed for chemically bound clusters. This is important for cluster assays: the use of this actuation scheme is likely to lead to a considerable increase of the signal-to-noise ratio of the assay and, thus, to the sensitivity of the assay itself. In addition, unspecific clusters and small clusters that are exposed to this actuation scheme are not stable. In all the experimental conditions described previously the breaking of such clusters was observed. It is quite remarkable that clusters "trapped" within bigger clusters are still rotating.

FIG. 7a shows a schematic sketch of a part of an apparatus according to a preferred embodiment of the present invention. The means 10 for applying a rotating magnetic field comprises twelve circularly arranged magnetic coils 11 and a central hole 13 for accommodating a sample cell. The sample cell 12, made e.g. from PMMA, has a hole 15 of 1 mm diameter for accommodating a sample fluid 14 with the analyte and the superparamagnetic particles. The sample cell 12 exactly fits into the hole 13. Although twelve magnetic coils are shown in FIG. 7a, only four of them were used in the actual experiment. However, it should be apparent that other actuation schemes may be applied by using more or less magnetic coils.

Figure 7B:
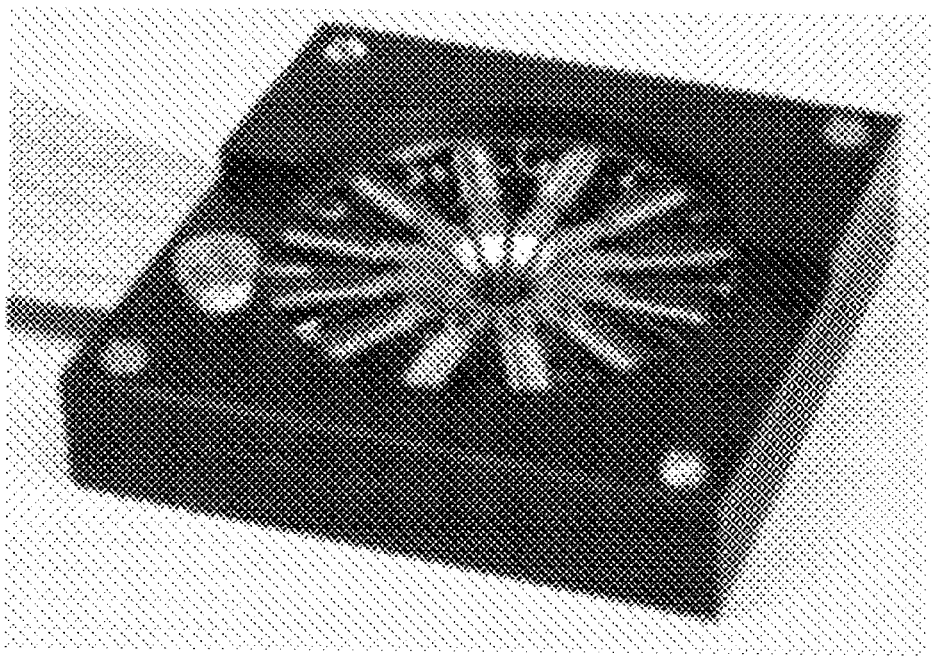

FIG. 7b shows a photograph of the apparatus schematically sketched in FIG. 7a.

In one exemplary experiment, superparamagnetic beads of 1 μm in diameter, covered with streptavidin (Dynabeads MyOnes™ from Invitrogen) have been used. They have been incubated with biotinylated BSA (a protein covered with biotin, which is specifically recognized by streptavidin). The buffer liquid used was PBS (a solution containing different salts and water). Once the sample was in place and the clusters have been formed the four magnetic coils were used to create a rotating magnetic field as described above. The clusters started to rotate and were observed with a high-speed camera, e.g. from below. The minimum value of the magnetic field was about 0.1 to 0.2 mT and the maximum value was chosen around 1 to 2 mT. The rotation frequency was set between 0.5 and 10 Hz. Since the buffer liquid consists basically of water, the viscosity was always 0.001 Pa s.

Figure 8:
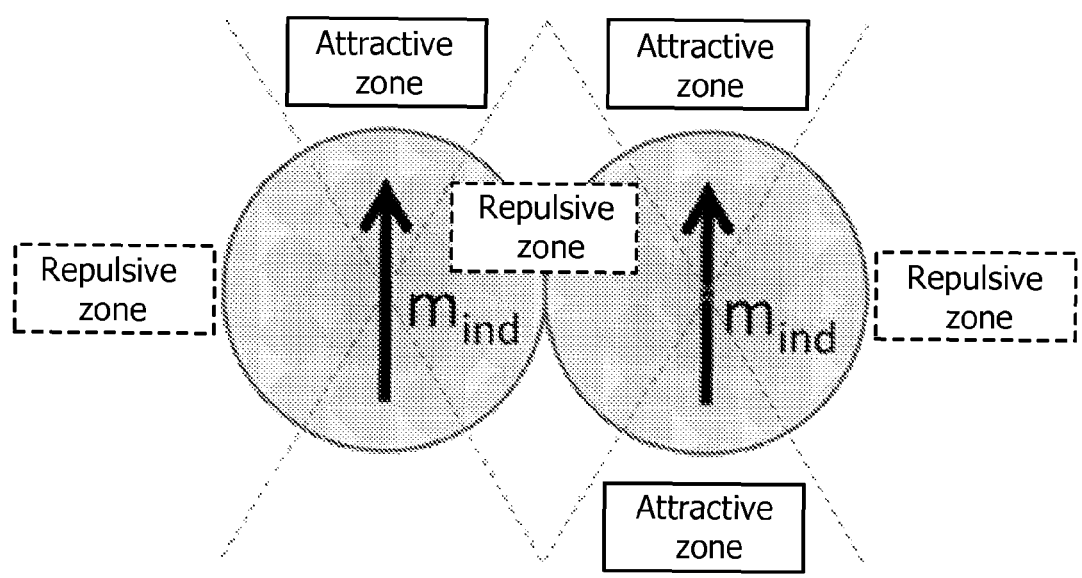
FIG. 8 shows a schematic side view of a cluster of two magnetic beads indicating a magnetic moment induced at the beads, and the resulting forces creating attractive and repulsive areas around the cluster.

FIG. 8 shows a schematic side view of a cluster 20 consisting of two magnetic beads next to each other. A bioactive agent is applied (not shown) which connects to an analyte generating a binding between the analyte and the magnetic bead, as is known in the state of the art. A magnetic field is applied as described inducing a magnetic moment at the beads directed in one direction towards above, denoted as $m_{ind}$ and a corresponding arrow indicating the force direction. This effect is referred to as an alignment of the particles. The time passing until the cluster 20 is oriented in a way described is denoted as alignment time, which is roughly in the order of tens of milliseconds depending on the magnetic field applied. The oscillation frequency of the magnetic field is lower than 10 times the inverse of the alignment time of the cluster 20. The magnetic particles and therewith the cluster 20 is oriented in the direction facing upwards, and the resulting forces creating attractive and repulsive areas around the cluster, as indicated in FIG. 8 by attractive zones above and below the cluster 20 and repulsive zones besides the cluster 20.

The method according to the present invention provides several advantages. Only specific clusters respond to the external magnetic field so that these specific clusters can be detected with high sensitivity. The actuation does not show magnetic-field-driven formation of clusters during the actuation scheme. Detection can be performed both in the bulk and on a surface. Thus, the biological reactions can be preformed in the bulk of the liquid, which is advantageous for assay simplicity, speed of the assay and costs. Finally, unspecific clusters are not stable and tend to break.

The detection of the clusters 20 of beads can be done by different technologies known in the state of the art. One detection technology is optical detection, for example described in the WO2008-072156.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A method of performing a cluster assay comprising the steps of:
   a) providing a suspension of superparamagnetic particles in a fluid to be analyzed, wherein the superparamagnetic particles are coated with a bioactive agent;
   b) allowing the particles to form clusters due to an analyte present within the fluid;
   c) selectively actuating clusters of superparamagnetic particles by applying an at least partially rotating magnetic field (B), wherein only clusters up to a predetermined size are rotated by the rotating magnetic field (B), and
   d) detecting the selectively actuated clusters within a background of other magnetic particles.

2. The method according to claim 1, wherein the step of selectively actuating clusters comprises selectively rotating clusters.

3. The method according to claim 1, wherein only clusters consisting of two particles are rotated by the rotating magnetic field.

4. The method according to claim 1, wherein the ratio between the maximum and minimum amplitudes of the magnetic field is between 1.1 and 10.

5. The method according to claim 1, wherein the oscillation frequency of the magnetic field is lower than the inverse of the time for the clusters to align.

6. An apparatus for performing a cluster assay comprising:
   a) means (12, 15) for accommodating a sample (14); and
   b) means (1 to 4; 11) for applying an at least partially rotating magnetic field (B), the magnetic field being adapted for selectively actuating clusters of superparamagnetic particles within a background of other magnetic particles), wherein only clusters up to a predetermined size are rotated by the rotating magnetic field (B).

7. The apparatus according to claim 6, wherein the means for applying a rotating magnetic field comprises a quadrupole configuration of four magnetic coils (1, 2, 3, 4).

8. The apparatus according to claim 6, wherein the ratio between the maximum and minimum amplitudes of the magnetic field is between 1.1 and 10.

9. The method according to claim 1, wherein the ratio between the maximum and minimum amplitudes of the magnetic field is between 2 and 8.

10. The method according to claim 1, wherein the ratio between the maximum and minimum amplitudes of the magnetic field is between 4 and 6.

11. The apparatus according to claim 6, wherein the ratio between the maximum and minimum amplitudes of the magnetic field is between 2 and 8.

12. The apparatus according to claim 6, wherein the ratio between the maximum and minimum amplitudes of the magnetid field is between 4 and 6.

13. A method of performing a cluster assay comprising the steps of:
   a) providing a suspension of superparamagnetic particles in a fluid to be analyzed, wherein the superparamagnetic particles are coated with a bioactive agent;
   b) allowing the particles to form clusters due to an analyte present within the fluid;
   c) selectively actuating clusters of superparamagnetic particles by applying an at least partially rotating magnetic field (B), and d) detecting the selectively actuated clusters, wherein the oscillation frequency of the magnetic field is lower than the inverse of the time for the clusters to align.

14. The method according to claim 13, wherein the step of selectively actuating clusters comprises selectively rotating clusters.

15. The method according to claim 14, wherein only clusters up to a predetermined size are rotated by the rotating magnetic field.

16. The method according to claim 15, wherein only clusters consisting of two particles are rotated by the rotating magnetic field.

17. The method according to claim 13, wherein the ratio between the maximum and minimum amplitudes of the magnetic field is between 1.1 and 10.

* * * * *